United States Patent [19]

Nielinger et al.

[11] Patent Number: 5,233,037
[45] Date of Patent: Aug. 3, 1993

[54] PRODUCTION OF CAPROLACTAM BY THERMAL DEPOLYMERIZATION OF POLYAMIDE 6

[75] Inventors: Werner Nielinger, Krefeld; Edgar Ostlinning, Duesseldorf; Karsten-Josef Idel, Krefeld; Dieter Freitag, Krefeld; Hans-Josef Buysch, Krefeld, all of Fed. Rep. of Germany

[73] Assignee: Bayer Aktiengesellschaft, Leverkusen, Fed. Rep. of Germany

[21] Appl. No.: 930,365

[22] Filed: Aug. 17, 1992

[30] Foreign Application Priority Data

Aug. 30, 1991 [DE] Fed. Rep. of Germany ....... 4128788
Apr. 7, 1992 [DE] Fed. Rep. of Germany ....... 4211609

[51] Int. Cl.⁵ ................. C07D 201/12; C07D 201/16
[52] U.S. Cl. ..................... 540/540; 540/485
[58] Field of Search ......................... 540/540

[56] References Cited

U.S. PATENT DOCUMENTS

Re. 25,640  9/1964  Braun et al. .......... 540/540
4,683,305  7/1987  Fuchs et al. .......... 540/540

FOREIGN PATENT DOCUMENTS 143502  11/1971  Czechoslovakia .......... 540/540
0048340  3/1982  European Pat. Off. ....... 540/540
0209021  1/1987  European Pat. Off. ....... 540/540
851194  10/1952  Fed. Rep. of Germany ..... 540/540
910056  4/1954  Fed. Rep. of Germany ..... 540/540
52-108991  11/1977  Japan .

OTHER PUBLICATIONS

Dmitrieva et al. "Translated from Khimicheskie Volokna", vol. 17, No. 7 pp. 5–12 (1985).
Derwent Data Base, JP 50 035 183, Apr. 3, 1975.
Chem. Ing. Technik, Bd. 45, Nr. 24, pp. 1509–1524, (1973).
Chemical Abstracts, 71:49329, (1969).
Chem. Abstr. 88:51715m (1978).
Chem. Abstr. 84:18020a (1976).

Primary Examiner—Robert T. Bond
Attorney, Agent, or Firm—Connolly & Hutz

[57] ABSTRACT

The invention relates to a process for the production of caprolactam by thermal depolymerization of polyamide in the presence of small quantities of potassium carbonate at 250° to 320° C. and to a process for purifying the resulting caprolactam.

5 Claims, No Drawings

PRODUCTION OF CAPROLACTAM BY THERMAL DEPOLYMERIZATION OF POLYAMIDE 6

This invention relates to a process for the production of caprolactam by thermal depolymerization of polyamide 6 in the presence of small quantities of potassium carbonate at 250° to 320° C. and to a process for purifying the resulting caprolactam.

By virtues of their favorable technological properties, thermoplastic polyamides are used as raw materials for commercial shaped articles, fibers and films. The range of application of the shaped articles can be increased by the addition of glass fibers, fillers or impact modifiers.

To reduce the quantities of plastic waste, there is an increasing demand for the raw materials from used parts to be reused either by reworking into new shaped articles or by depolymerization into the monomers and re-polymerization.

Processes for the degradation of polyamide 6 to caprolactam have long been known. The depolymerization reaction takes place in the presence of acidic or basic catalysts at elevated temperature, often in the presence of steam. Phosphoric acids and alkali metal salts thereof, bases, such as sodium hydroxide, sodium carbonate and potassium hydrogen carbonate, but not potassium carbonate, are mentioned as catalysts for the process of Japanese patent 50 035-183. In this process, however, the yield of caprolactam is less than 50%.

An industrial-scale version of the depolymerization process is described in Chem. Ing. Techn. 45, 1510 (1973). In this process, the polyamide is depolymerized with superheated steam at elevated temperature in the presence of a catalyst in a tank reactor. The mixture of caprolactam and water formed is concentrated and purified by an oxidizing agent. Finally, the lactam is rectified. The oxidation may be carried out with hydrogen peroxide, sodium hypochlorite or potassium permanganate in the presence of calcium oxide (JP 52 108-991).

According to European patent 209 021, oligomers of caprolactam may be depolymerized in a fluidized bed using aluminium oxide as catalyst. Even after distillation, the caprolactam obtained by this process has to be further purified together with purified caprolactam from Beckmann's rearrangement.

It has now been found that a caprolactam can be obtained in a high yield when depolymerization of the polyamide is carried out with potassium carbonate as catalyst and the caprolactam is distilled off in vacuo.

Accordingly, the present invention relates to a process for the product of $\epsilon$-caprolactam from polyamide 6 by depolymerization, in which the polyamide is heated in an inert gas atmosphere, preferably of nitrogen, to temperatures of 250° to 320° C. and preferably to temperatures of 270° to 300° C. in the presence of 0.5 to 2.5% by weight potassium carbonate and the caprolactam eliminated is distilled off under a reduced pressure of $\leq 100$ mbar, preferably 15 to 100 mbar and, more preferably, 20 to 90 mbar and the caprolactam distilled off is fractionated once more, optionally in the presence of additives.

Surprisingly, the use of potassium carbonate instead of sodium carbonate considerably increases the depolymerization rate of polyamide 6 and the yield of caprolactam. It is thus possible to reduce the temperature for the same throughput which results in a lighter colored and less contaminated product. After fractionation, this product may be reused for the production of high molecular weight polyamides without oxidation with potassium permanganate. Since neither water nor steam is added during the depolymerization process, there is no need for the removal of water before or during fractionation of the caprolactam.

The process can also be applied to polyamide 6 containing glass fibers and fillers and also to products containing impact modifiers.

In the context of the invention, polyamide 6 is understood to be pure polyamide 6 and also polyamides of which more than 50% by weight and preferably more than 80% by weight are based on polyamide 6.

In the process according to the invention $\epsilon$-caprolactam is obtained in a high yield, although it may require further purification for reaction to form high molecular weight polyamides. Purification processes for lactams are known, such as for example oxidation of aqueous lactams are known, such as for example oxidation of aqueous lactam solutions with potassium permanganate (JA 52108-991) or fractional distillation using acids or bases (DE 745224). These processes are costly and complicated and do not always produce satisfactory results. For example, in the polymerization of $\epsilon$-caprolactam obtained by thermal depolymerization of non-modified polyamide 6 a relative viscosity of only 2.3 is obtained which may increase to 3.5 after the distillation of the lactam using phosphoric acid. These products are not suitable for the production of very high molecular weight polyamides.

It has been found that it is possible to obtain $\epsilon$-caprolactam which can be reacted to form high molecular weight polyamides with a relative viscosity of $>3.5$ without any further purification steps if the eliminated $\epsilon$-caprolactam is distilled out of the reaction mixture in vacuo immediately after its formation until the distillate contains no more than 0.2, and preferably no more than 0.03 mmol, of basic constituents in one gramme of distillate. The determination of the basic constituents is carried out by acid-base titration of the lactam distillate with HCl.

The invention thus also relates to a process for the production of highly pure $\epsilon$-caprolactam from polyamide 6, characterized in that the $\epsilon$-caprolactam obtained in the above-described depolymerization process is distilled off immediately after its formation at a reduced pressure of $\leq 100$ mbar, and preferably 15 to 100 mbar, and particularly preferably at 20–90 mbar, until the distillate contains no more than 0.2, and preferably no more than 0.03 mmol, of basic constituents in one gramme of distillate.

This result is also surprising and was not predictable since the fractional distillation of $\epsilon$-caprolactam obtained by thermal depolymerization results in a polyamide with a relative viscosity of no more than 2.5, which is thus not suitable for many practical applications.

The determination of the basic constituents is carried out by acid-base titration of an approximately 2% aqueous solution of the $\epsilon$-caprolactam distillate with 1N hydrochloric acid using a Mettler titrator DL 25.

The invention also relates to the use of the highly pure $\epsilon$-caprolactam produced by the process according to the invention for the production of polyamides with a high molecular weight and a relative viscosity of $>3.5$, characterized in that the $\epsilon$-caprolactam obtainable from the process is polymerized directly without any further purification stages.

EXAMPLE 1

In a round-bottomed flask, 40 g polyamide 6 having a relative viscosity of 3.1 (as measured on a 1% solution in m-cresol at 25° C. in an Ubbelohde viscosimeter) and 0.86 g potassium carbonate (2.15%) are heated under nitrogen to 320° C. (bath temperature). The melt is stirred and, after reaching the bath temperature, the pressure is reduced in steps to 25 mbar. The caprolactam begins to distill off at around 60 mbar and distillation is terminated after about 30 minutes. A colorless distillate is obtained in a yield of 92%. If 0.43 g potassium carbonate (1.08%) is used, a time of about 55 minutes is required for distillation.

EXAMPLE 2

In a stirred tank reactor of stainless steel, a mixture of 2.1 kg polyamide 6 having a relative viscosity of 3.1 and 36.3 g potassium carbonate are heated by means of a heat-transfer medium having a temperature of 320° C. After the temperature of the polyamide melt has reached 290° C., the caprolactam formed is distilled off in vacuo.

A colorless, 97–98% pure distillate, which is fractionated once more, is obtained in a yield of 95%.

EXAMPLE 3

150 g of polyamide 6 having a relative viscosity of 3.1 (measured in an Ubbelohde viscosimeter at 25° C. using a 1% solution in m-cresol) and 2.59 g of potassium carbonate are heated to 300° C. (bath temperature). 5 minutes after this temperature is reached the vessel is carefully evacuated while intensively stirring the melt. In the course of 80 to 90 minutes a colorless distillate is obtained at 18 mbar in a yield of 93%. The distillate contains 0.17 mmol of base per gramme of distillate.

Hydrolytic polymerization of the distillate produces an almost colorless polyamide with a relative viscosity of 2.4.

EXAMPLE 4

Example 4 demonstrates the dependence of the formation of basic products on time. If the depolymerization of polyamide 6 is carried out as described in example 3, but with the difference that the melt is kept at 300° C. for one hour until the vacuum is applied, a content of basic constituents of 0.24 mmol/g is obtained. The relative viscosity of a polyamide obtained therefrom is 2.2.

EXAMPLE 5

Example 3 is repeated with the distinction that the distillate is subjected once again to fractional distillation prior to hydrolytic polymerization. The content of basic constituents in the distillate is only slightly less after fractionation. The relative viscosity of the polyamide produced from the fractionated $\epsilon$-caprolactam is 2.5.

EXAMPLES OF HIGHLY PURE $\epsilon$-CAPROLACTAM

EXAMPLE 6

Example 3 is repeated with the distinction that during the depolymerization process the first distillate quantity of 40 g is removed and hydrolytic polymerization is carried out without any further purification of the $\epsilon$-caprolactam, as described in comparative example 1. Using hydrochloric acid, 0.0086 mmol of base was detected in 1 g of distillate. The polyamide produced therefrom is a colorless product having a relative viscosity of 4.5. In the hydrolytic polymerization of commercially available $\epsilon$-caprolactam a polyamide with a relative viscosity of 4.5 is also obtained under comparable conditions.

EXAMPLE 7

Example 6 is repeated, except that the $\epsilon$-caprolactam is collected until the distillate consumes 0.016 mmol of hydrochloric acid per g of distillate in the titration.

After hydrolytic polymerization of the lactam a colorless polyamide with a relative viscosity of 4.0 is obtained.

We claim:

1. A process for the production of $\epsilon$-caprolactam by depolymerization of polyamide 6 by alkali-catalyzed depolymerization, characterized in that the polyamide 6 is heated with 0.5 to 2.5% by weight potassium carbonate to 250° to 320° C. in an inert gas atmosphere and the $\epsilon$-caprolactam eliminated is distilled off under a reduced pressure of $\leq 100$ mbar and the distillate is fractionated.

2. A process for the production of caprolactam as claimed in claim 1, characterized in that glass-fiber-containing or filler-containing polyamide 6 or impact-modified polyamide 6 is used.

3. A process as claimed in claim 1, characterized in that 0.5 to 2.15% by weight potassium carbonate is used and/or the polyamide 6 is heated to 265°–300° C. and/or the $\epsilon$-caprolactam eliminated is distilled off at 12 to 100 mbar.

4. A process as claimed in claim 1, characterized in that the polyamide 6 is heated with 0.5 to 2.0% by weight potassium carbonate to 265°–300° C. in a nitrogen atmosphere and the -caprolactam eliminated is distilled off at 20–80 mbar and the distillate is fractionated.

5. A process for the production of $\epsilon$- caprolactam by depolymerization of polyamide 6 by heating the polyamide with 0.3 to 10% by weight potassium carbonate to 250°–300° C. under reduced pressure, characterized in that the $\epsilon$-caprolactam is distilled off immediately after it is formed so that its content of bases is no more than 0.2, and preferably no more than 0.03 mmol/g distillate.

* * * * *